(12) United States Patent
Olstad (10) Patent No.: US 6,447,450 B1
(45) Date of Patent: Sep. 10, 2002

(54) ECG GATED ULTRASONIC IMAGE COMPOUNDING

(75) Inventor: Bjørn Olstad, Stathelle (NO)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/432,899

(22) Filed: Nov. 2, 1999

(51) Int. Cl.$^7$ .................................................. A61B 8/00
(52) U.S. Cl. ........................................ 600/437; 600/443
(58) Field of Search ................................ 600/443, 447, 600/438, 437, 448, 449, 455, 444, 446; 601/437

(56) References Cited

U.S. PATENT DOCUMENTS

| | | | |
|---|---|---|---|
| 5,099,847 A | | 3/1992 | Powers et al. |
| 5,476,096 A | | 12/1995 | Olstad et al. |
| 5,585,945 A | * | 12/1996 | Ikeda et al. .................. 358/540 |
| 5,731,811 A | * | 3/1998 | De Lange et al. .......... 345/201 |
| 6,117,081 A | * | 9/2000 | Jago et al. ................... 600/443 |

* cited by examiner

Primary Examiner—Marvin M. Lateef
Assistant Examiner—Maulin Patel
(74) Attorney, Agent, or Firm—McAndrews, Held & Malloy, Ltd.; Peter J. Vogel; Michael A. Dellapenna (57) ABSTRACT

An ECG gated ultrasonic imaging compounding system and method for synthesizing a cineloop of a compound ultrasonic image such as a cardiac cycle is presented. In real-time operation, a series of image frames may be recorded at a frame rate over a cardiac cycle and stored in a cineloop memory. A second series of image frames are recorded over a second cardiac cycle. The image frames of the second cardiac cycle are frame-by-frame aligned in time and space with the corresponding image frames from the cineloop memory. The aligned frames are then combined to form a series of synthesized image frames which then replace the original image frames in the cineloop memory. Subsequent series of image frames are also combined with the synthesized image frames in the cineloop memory to form new synthesized image frames which then replace the old synthesized image frames in the image array, and so forth. The series of image frames may be triggered to begin at a cardiac event such as the R-event.

63 Claims, 7 Drawing Sheets

HEARTBEAT A | HEARTBEAT B | NOT ALIGNED COMBINATION OF A AND B

ECG GATED ULTRASONIC IMAGE COMPOUNDING

CROSS REFERENCE TO RELATED APPLICATIONS

Not applicable

STATEMENT REGARDING FEDERALLY SPONSORED RESEARCH & DEVELOPMENT

Not applicable

BACKGROUND OF THE INVENTION

The underlying image quality is an important aspect of a medical ultrasound imaging scanner. Throughout the field, there is a constant effort to improve image quality. However, ultrasound imaging remains a modality that is very patient dependent. The ultrasonic imaging and detection of important pathological phenomena may fail if the image is not of sufficient quality to assure diagnosis.

In addition to image quality limitations, there are physiological effects that may impact ultrasonic imaging. For example, small variations between consecutive heartbeats may adversely impact imaging and image quality. These beat to beat variations may be caused by may factors including: respiration, heartrate variations, double systoles, early excitations and a number of other physiological effects. These variations present a limitation for performing both repeatable and reproducible measurements of ultrasound derived parameters such as blood flow velocities, wall motion or wall thickening, for example.

Because of the difficulties inherent in performing repeatable ultrasonic measurements, several measurement protocols have been developed wherein an ultrasonic imaging operator is instructed to repeat the same measurement for a certain number of consecutive heartbeats and report the average value. These measurement protocols improve the repeatability and reproducibility of the measurement because an average measurement is reported, rather than a single measurement which may not represent a normal heartbeat.

The prior art describes techniques for temporal processing of ultrasound data to reduce noise. These techniques include consecutive measurements at a given location which are combined in order to reduce noise. However, the problem with these techniques in cardiac imaging is that the imaged organ is moving. That is, as the heart beats, it changes its state in terms of blood flow pattern, cavity shapes, wall motion and wall thickness, for example. Because the imaged organ is moving and changing, simple temporal processing techniques are ineffective and the techniques of the prior art yield images of unacceptable image quality. The same limitations on imaging of the heart also apply to other organs and vessels that move or change. Many organs may change according to respiration or blood pulsation, for example. As a result, when using temporal processing, the dynamics and image quality of the imaged organ are degraded as a side effect of the temporal averaging.

The prior art also describes techniques for temporal processing of ultrasound data to increase frame rate. For example, U.S. Pat. No. 5,099,847 issued to Powers et al. describes a techniques for increasing the display frame rate of a medical ultrasound imaging system. The system generates a trigger signal based on a predetermined event in the subject's cardiac cycle. The system produces a first series of image frames in response to a first trigger signal during a first cardiac cycle and a second series of image frames in response to a second trigger signal during a second cardiac cycle. The image frames of the first and second series are then interleaved in the order of occurrence in the cardiac cycle to produce a frame rate twice as great as the imaging frame rate. The Powers patent thus relies on frame recordings at different instants in the first and second cardiac cycles in order to obtain a merged sequence of images with a higher frame rate. However, while the Powers patent may provide a higher frame rate, the sequenced images are taken from different cardiac cycles. Because the images are taken from different cardiac cycles, one or more of the cycles may be affected by artifacts induced from, for example, respiration. Additionally, the subject's position or the probe's position may have moved from one cardiac cycle to another. Interleaving frames from cardiac sequences affected by motion may yield a jittery and inaccurate combined image sequence which may adversely affect diagnosis.

Thus, a need has long existed for an improved ultrasonic imaging system that provides improved ultrasonic images that maximize repeatability and reproducibility, especially in cardiac and cardiac-influenced imaging. A need also exists for an ultrasonic imaging system that provides a clear, easily diagnosable image that represents an accurate image through a cardiac cycle and minimizes adverse imaging effects such as respiration effects and movement effects.

BRIEF SUMMARY OF THE INVENTION

The present invention synthesizes a cineloop of a compounded ultrasonic image, such as over a cardiac cycle, for example. In a real-time example, a series of image frames is recorded over a cardiac cycle and stored in an image array. A second series of image frames are recorded over a second cardiac cycle. The image frames of the second cardiac cycle are then temporally and spatially aligned with the image frames of the first cardiac cycle. The first and second series of image frames at then combined to form a series of synthesized image frames which are then stored in the image array in place of the first series of image frames. Subsequent series of image frames are also combined with the synthesized image frames to form new synthesized image frames. The series of image frames may be triggered to begin at a cardiac event such as the R-event. An age attribute may also be assigned to the image frames for use in weighting the image frame during combination. Additionally, a mismatch error estimate between image frames may be determined. Image frames or cardiac cycles with a high mismatch error may not be combined, or alternatively, only a portion of cardiac cycles having the least mismatch error may be combined. In addition, a cineloop may be constructed based around the standard deviation of the image frames to display non-repetitive variations in the cardiac cycle.

These and other features of the preferred embodiments of the present invention are discussed or apparent in the following detailed description of the preferred embodiments of the present invention.

DETAILED DESCRIPTION OF THE INVENTION

The preferred embodiments of the present invention applies to any time motion, two-dimensional (2-D) or three-dimensional (3-D) ultrasound imaging with minor refinements presented below. The preferred embodiments of the present invention may be applied to any imaging mode including existing applications such as tissue/B-mode imaging, color flow imaging, angio/Power Doppler imaging, tissue motion or velocity imaging and strain rate imaging or time mode imaging, M-mode or PV or CV Doppler. The present invention may also be used to image many non-cardiac applications and may be especially useful where the imaged object has a periodic behavior that follows the cardiac cycle such as vascular and blood flow studies in various organs, for example.

Figure 1:
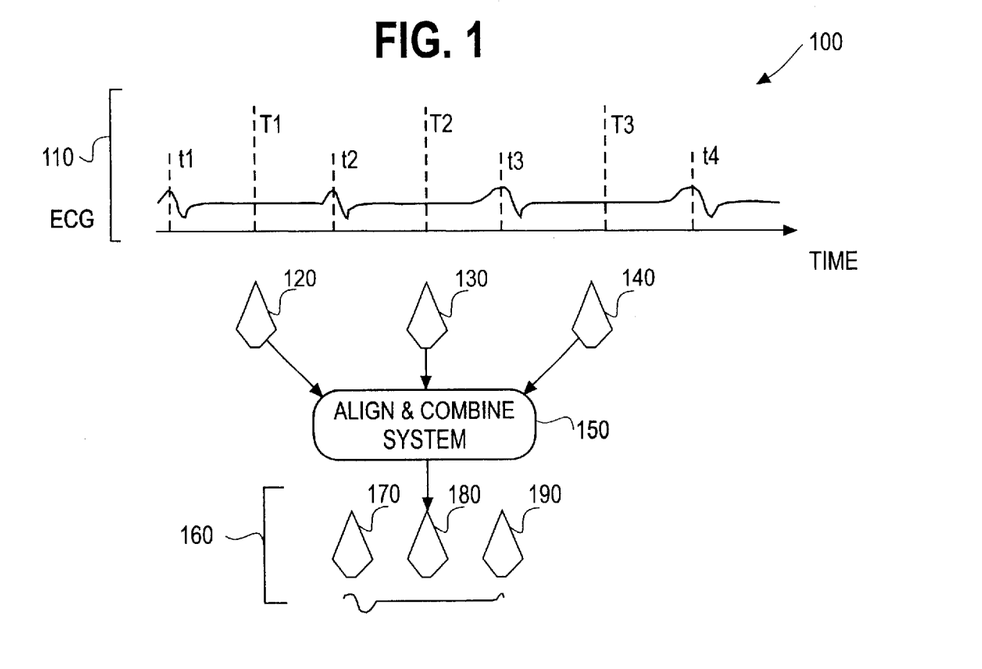
FIG. 1 illustrates an exemplary typical imaging sequence diagram according to a preferred embodiment of the present invention.

FIG. 1 illustrates an exemplary imaging sequence diagram 100 according to a preferred embodiment of the present invention for illustration. The imaging sequence diagram 100 includes an electrocardiograph (ECG) trace 110, three image frames 120–140, an align and combine system 150, and a cineloop 160 comprising of combined frames 170–190.

The electrocardiograph (ECG) trace 110 displays an ECG of three cardiac cycles or heartbeats. The ECG trace 110 includes four trigger events at times (t1, t2, t3 and t4). The trigger events are typically the R-event in the QRS complex (which is associated with ventricular systole), but other events such as the S-event may be employed. The ECG trace 110 also includes three sample events at times (T1, T2, and T3). At each sample event time in this example, a two-dimensional image frame 120–140 of the heart is formed.

The sample events at times (T1, T2, and T3) are selected to be the same time increment from the preceding trigger events at times (t1, t2, t3 and t4) so that the same phase of the cardiac cycle is imaged by each image frame. That is, by requiring (T1-t1)=(T2-t2)=(T3-t3), the three image frames 120–140 are recorded at the same time delay after the last R-event in the ECG trace. The three image frames 120–140 associated with times (T1, T2, and T3) are then spatially aligned and combined by the align and combine system 150 to form a single image frame 180, as will be discussed below. The combined image frame 180 forms a single frame of a cineloop 160 of the entire cardiac cycle.

Although FIG. 1 is illustrated with a single trigger event per heart cycle, in operation the ultrasonic system may continuously form image frames. The system may then determine, for each image frame, the corresponding phase of the cardiac cycle and then combine image frames of the same or similar phases in consecutive order to form cineloop image frames.

Figure 2:
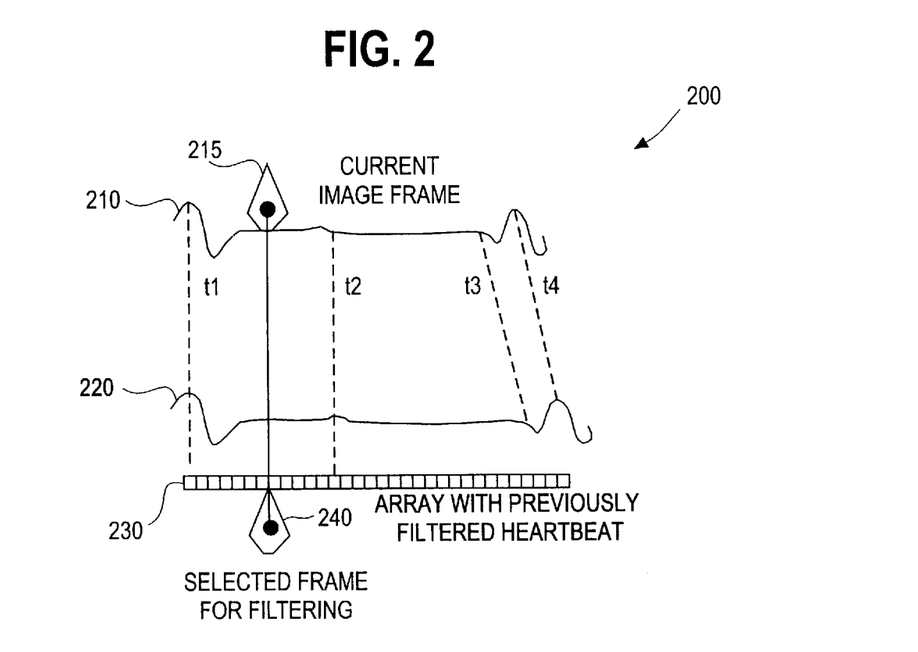
FIG. 2 illustrates a preferred implementation of the system for real-time ultrasonic imaging of a preferred embodiment of the present invention.

The system may operate upon both live, real-time images of cardiac cycles as well as upon a recorded sequence with multiple cardiac cycles. FIG. 2 illustrates a preferred implementation of a system for real-time imaging 200 according to a preferred embodiment of the present invention. FIG. 2 includes a current ECG trace 210 having a current image frame 215, a stored ECG trace 220, and an image array 230 comprised of a number of stored image frames. The image array 230 includes a selected frame 240 corresponding generally to the cardiac cycle phase of the current image frame 215.

The image array 230 includes a number image frames (indicated as squares in the array) stored in the cineloop and corresponding to various phases of the cardiac cycle. The image frames are formed at a rate called a frame rate. The frame rate may be selected up to the maximum system frame rate. The maximum frame rate is dependent upon the speed at which the underlying ultrasonic imaging system forms an image frame and may vary depending upon the type of image formed. For example, 3-D images generally take longer to form than 2-D images, consequently, the frame rate for a 3-D imaging system is lower. The image array 230 includes images obtained preferably starting at the R-event and generated thereafter at the corresponding selected frame rate. The image array 230 includes image frames covering a complete cardiac cycle. Depending upon the type of ultrasonic imaging desired, the image frames may be 2-D or 3-D frames of data, Doppler or spectral data M-mode data, or other ultrasonic data.

Initially, the image frames of the image array 230 may be image frames recorded during a first heart cycle. During a subsequent heart cycle, as new image frames are acquired, each new image frame is spatially and temporally aligned with one of the preceding image frames in the image array 230. The new image frame and an associated preceding image frame from the image array 230 are then synthesized to form a synthesized array image frame, as will be discussed below. The synthesized array image frame then replaces the old image frame from the image array. For example, in FIG. 2, a current image frame 215 is imaged. The phase of the current image frame 215 in the cardiac cycle of the current ECG trace 210 is determined based on the time from the most recent R-event or an estimate of the cardiac cycle duration based on the duration of the cineloop, as will be described below. An image frame in the image array 230 corresponding the similar phase in the cardiac cycle as the current image frame 215 is then selected. The selected frame 240 is then spatially aligned with the current image frame 215 and the two frames are combined to form a synthesized frame. The synthesized frame is displayed and stored in the image array 230 as an updated image frame.

A system for combining the current image frame 215 and the selected image frame 240 may be based on the system described in U.S. Pat. No. 5,476,095 to Olstad et al. The combining system may provide strong filtering to alleviate respiratory noise that may occur if a patient breathes while the probe is kept still. Additionally, the system of the Olstad patent may help avoid "ghost" images that may be caused by old image data in the image array 230 conflicting with new image data after a probe is moved to a new imaging location.

Because the cardiac cycle may vary in temporal length from cycle to cycle, depending upon the chosen time alignment mapping, not all images in the image array 230 may be updated during each cardiac cycle. Consequently, each image frame in the image array 230 may be assigned an age attribute corresponding to the length of time since the last update of the image frame. The image frame in the image array, when combined with a current image frame, may be weighted so that its weighting is reduced with increasing time since the last update of the image frame.

Figure 3:
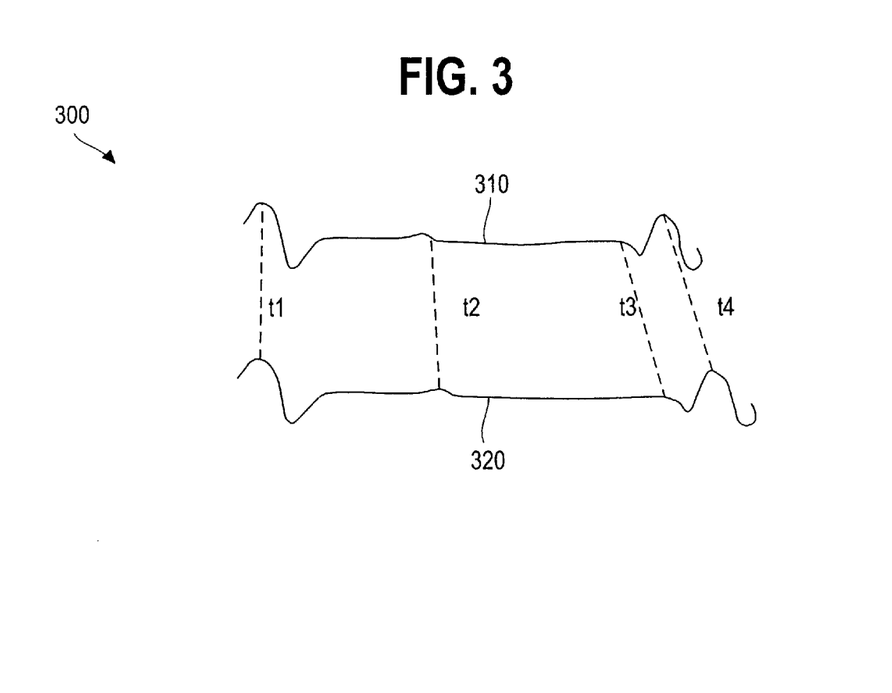
FIG. 3 illustrates the temporal alignment of a first cardiac cycle and a second cardiac cycle.

As mentioned above, at least one image frame having a similar cardiac cycle phase as an image frame in the image array 230 may be combined to form a single cineloop frame. Several exemplary methods may be utilized to accomplish the cardiac-phase or time alignment between frames of different cardiac cycles. FIG. 3 illustrates the time alignment 300 of a first cardiac cycle 310 and a second cardiac cycle 320. As mentioned above, a first exemplary method of aligning cardiac cycles includes 1) generating image frames over several entire cardiac cycles, 2) determining the time index for the R-event in the ECG trace, 3) determining the phase in the heart cycle of each frame based on the time difference between the frame and the most recent R-event, and 4) combining frames of the same or similar cardiac phases to form a combined frame. Alternatively, some phono-indication of a valve opening may be used as a time index instead of the R-event.

While the above method performs well for cardiac cycles of roughly the same time length, in practice the length of successive cardiac cycles may vary. However, similar cardiac cycle frames in each of the cardiac cycles must still be aligned to form a single frame in the cineloop. An alternative method of aligning cardiac cycles of varying time lengths is linear stretching of the cardiac cycles. As shown in FIG. 3, to perform linear stretching, several time points (t1, t2, t3 and t4) corresponding to various events in the cardiac cycle are determined in each cardiac cycle. The time points for the second cardiac cycle 320 may then be fit to the first cardiac cycle 310 and a conversion factor determined. The corresponding phases in each of the cardiac cycles may then be determined by reference to the linear stretching points. Linear stretching may be especially useful in clinical heart imaging because not all heart cycles are of the same length.

Linear stretching may also be accomplished as a piece wise linear stretching of multiple time intervals (e.g., t1 to t2, t2 to t3 and t3 to t4 in FIG. 2). Piecewise linear stretching is useful because the atrium contraction which occurs just prior to the last R-event may get a better time alignment if this period is aligned according to the time between the frame acquisition and the next trigger event. In addition, systole and diastole separation may be advantageous because the time variations that cause heart rate variations mainly affect diastole.

Finally, the cardiac cycles may be aligned through the use of traces or image derived parameters that are a function of time. These parameters may be directly correlated with a Viterbi algorithm, for example, in order to estimate an optimal data dependent map between events and frames in the two cardiac cycles Preferably, the systolic part of the cardiac cycle may, in all time alignment schemes, be matched approximately such that frames with the same delay from the most recent trigger events are combined. Also preferably, the ultrasound acquisition may be independent of trigger events or image continuously. This means that there may be a jitter or mismatch between the R-event and the first acquired image frame because the R-event is not being used at a trigger event. This mismatch is between 0 and the time required for acquiring a single image frame. The time alignment can hence be improved if the ultrasound acquisition can be aborted when a trigger event is detected and then restarted at a fixed delay after the occurrence of the trigger event. Such a triggered reset of the acquisition would give perfect time alignment even in situations with low frame rates.

Figure 4:
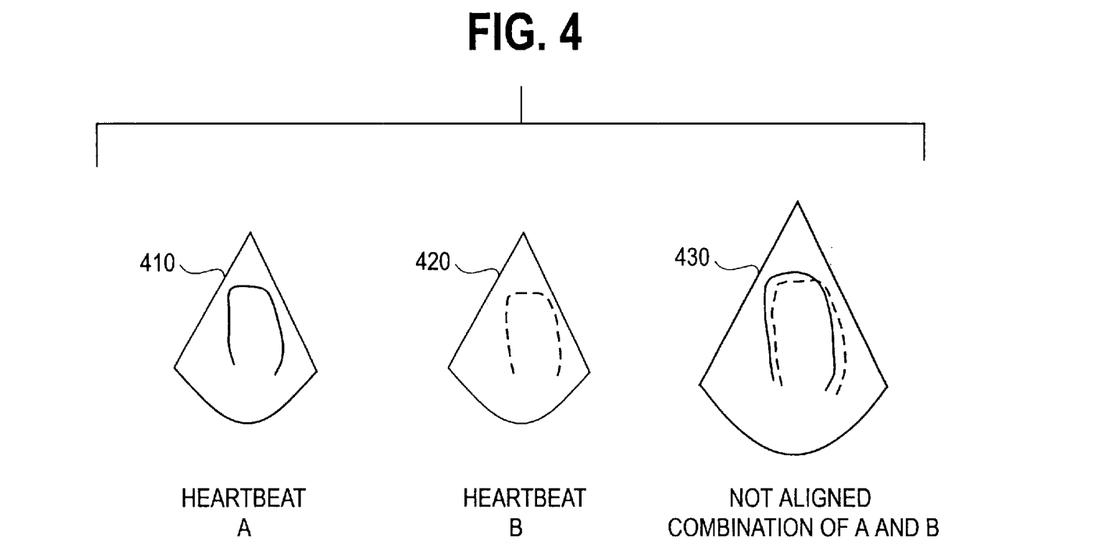
FIG. 4 illustrates the spatial mismatch between two image frames; an image frame from heartbeat A and an image frame from heartbeat B.

The image frame selected from heart cycles after time alignment may not necessarily spatially match perfectly pixel by pixel with an image frame from the image array 230. The spatial mismatch may be caused by several factors such as respiration, probe movement by the operator, and so forth. FIG. 4 illustrates the spatial mismatch between two image frames; an image frame from heartbeat A 410 and an image frame from heartbeat B 420. When the two image frames 410, 420 are superimposed to form a combined frame 430, the spatial mismatch is clearly evident. The spatial misalignment may be reduced if one of the images is translated with an offset in the X and Y directions before the images are combined to form a frame in the cineloop. Several algorithms exist and are known for automatic alignment of images. One possibility is to select the X and Y offsets that minimize the square error between the images. It may be advantageous to base this error computation on the tissue image even in color modalities if the tissue component carries more robust geometrical information. Matching algorithms also exist in the literature for more complex image warping models such as combined translation/rotation and locally varying transformations.

In addition, raw ultrasound information is usually represented in a polar format internally in many ultrasound scanners. The polar format represents the image as a function of range and lateral angle. The polar format may therefore be a useful representation for implementation of efficient space alignment algorithms.

Figure 5:
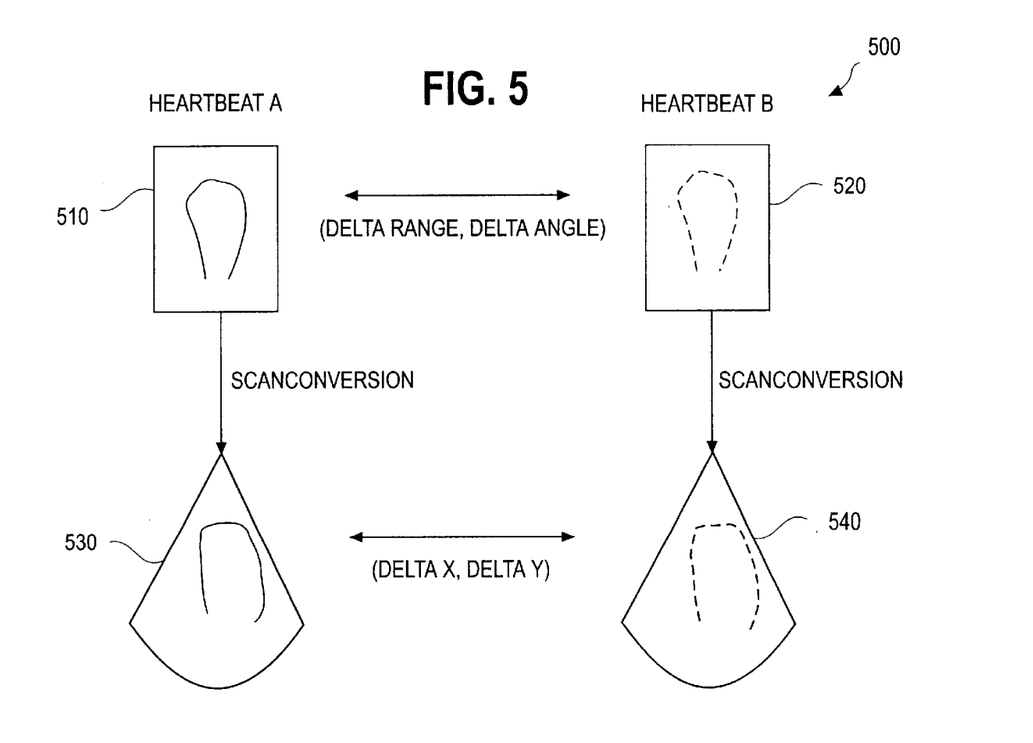
FIG. 5 illustrates a comparison of performing a spatial alignment of two image frames using Cartesian and Polar coordinates.

FIG. 5 illustrates the comparison 500 of performing a spatial alignment of two frames using Cartesian and Polar coordinates. FIG. 5 includes a polar coordinate Heartbeat A 510, a polar coordinate Heartbeat B 520, a Cartesian coordinate Heartbeat A 530, and a Cartesian coordinate Heartbeat B 540. Conversion from polar geometry to Cartesian or rectangular geometry is generally referred to as scan conversion. Instead of performing spatial alignment to derive X and Y offsets in the Cartesian images, spatial alignment may be performed in the polar domain to derive range and lateral offsets. Because of the differences in the Cartesian and polar domain representations and the spatial fitting method chosen, the resultant Cartesian and polar spatial alignments may not necessarily be identical. While the Cartesian domain may be more desirable for some imaging formats, processing in the polar domain may potentially yield a more accurate spatial alignment in some imaging formats. For example, when imaging apical cardiac views, processing in the polar domain may be preferable.

Figure 6:
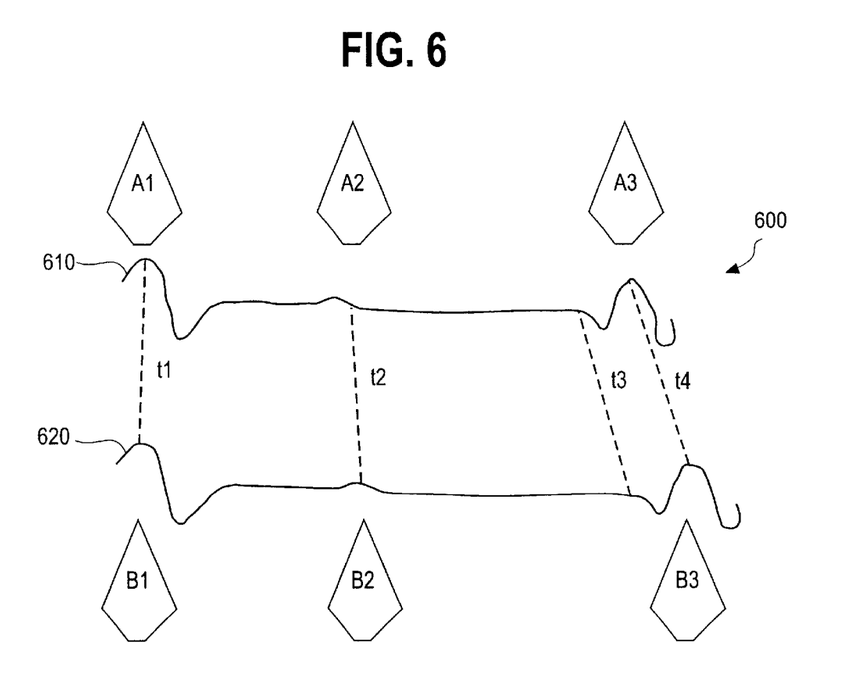
FIG. 6 illustrates a method for reducing the number of image frames processed to spatially align all image frames of two cardiac cycles in accordance with a preferred embodiment of the present invention.

FIG. 6 illustrates a method 600 for reducing the number of image frames processed to spatially align all image frames of two cardiac cycles. Cardiac cycle A 610 includes three image frames A1, A2, and A3, The image frames A1, A2, and A3 are preferably imaged at or near significant cardiac events in the cardiac cycles such as the R-event and the S-event. Cardiac cycle B 620 also includes three image frames B1, B2, and B3 preferably images at or near significant cardiac events. Spatial misalignment does not vary rapidly from frame to frame throughout the cardiac cycle. Thus, by spatially aligning image frames in the two cardiac cycles 610, 620 at the cardiac events, the spatial alignments for the remaining image frames in the two cardiac cycles 610, 620 may also be determined. For example, once the spatial alignment for the two cardiac cycles has been determined at the R-event and possibly for the end of systole, the determined spatial alignments may be used to generate spatial translation parameters for the spatial alignment of all the image frames in the two cardiac cycles 610, 620. The spatial alignment parameters determined for the selected frames may, for example, be interpolated in the temporal domain to determine spatial alignment parameters for all image frames. The interpolation of spatial alignment for all image frames may be performed in a much shorter time than performing the actual spatial alignment for all image frames.

The present invention may be applied both to live, real-time imaging and to recorded ultrasonic sequence imaging. For performing recorded ultrasonic sequence imaging, an image sequence usually 3–10 seconds in length is recorded during which the ultrasonic probe remains in a single position. The cardiac cycles of the recorded image sequence may then be analyzed and processed. Alternatively, the user may specify the number of cardiac cycles to be recorded in the image sequence. Clinically, the patient is typically instructed to breathe our and wait. Once the patient has completed breathing out, the system images several heart cycles and then ceases imaging, at which point the patient begins breathing again normally. The captured heart cycles are then typically processed and analyzed.

Preferably, the cardiac cycles that are synthesized to form the cineloop are typical cardiac cycles and not irregular or atypical. Irregular or a-typical cardiac cycles may skew the diagnostic value of the cineloop and usually offer little insight into the state of the heart during the cardiac cycle. Thus, when a cardiac cycle is determined to be an atypical cardiac cycle, it is not included in the cineloop. A cardiac cycle may be determined to be atypical in a number of ways. For example, large variations in heart rate, large variations in respiration, or a poor match of image data in an image frame may each cause a cardiac cycle to be judged atypical and consequently not included in the cineloop.

When large variations in heart rate between two cardiac cycles occur, temporal alignment of the cardiac cycles is difficult for many reasons. For example, because image frames are recorded at a constant rate, a typical cardiac cycle may have ten image frames while a high heart rate cardiac cycle may only have five, for example which may greatly complicate temporal alignment. Additionally, in a high heart rate cardiac cycle the time offset of an image frame from a cardiac event may be significant when compared to the overall time for the cardiac cycle.

Large variations in respiration may affect the spatial alignment of the image frames between two cardiac cycles. For example, the depth within the body of a particular cardiac feature may differ when the patient's lungs are fully expanded as compared to when the lungs are not expanded. Variations in respiration may be minimized by instructing the patient to control respiration during imaging. Additionally, respiration effects may be determined from an ECG signal as a low-pass component of the ECG signal.

Once the image frames of two cardiac cycles have been temporally and spatially aligned, an estimator may be employed to generate an estimate of the time and space mismatch between the two cardiac cycles. The estimator may determine a mismatch error estimate as the sum of the square error between each pair of time aligned image frames, for example. Cardiac cycles having a high mismatch error estimate are determined to be atypical cardiac cycles and are excluded from the cineloop. Alternatively, if the cineloop is constructed from recorded cardiac cycles, the cardiac cycles having the lowest mismatch estimate may be selected for forming the cineloop. For example, the cineloop may be constructed using the half of the available cardiac cycles, the selected cardiac cycles having the lowest mismatch estimate. Additionally, the mismatch estimate may be performed prior to spatial alignment. If the mismatch estimate is large, the cardiac cycle is not included in the cineloop and the actual spatial alignment of the cardiac cycle need not be performed.

Additionally, the cardiac cycles selected for inclusion in the cineloop may be weighted based on mismatch estimate when included in the cineloop. For example, cardiac cycles having a high mismatch estimate may be weighted less and cardiac cycles having a low mismatch error estimate may be weighted more. Additionally, especially when performing real-time imaging, cardiac cycles may be weighted by age. Thus, more recent cardiac cycles may receive a higher weighting and less recent cardiac cycles may receive a lower weighting.

Alternatively, the mismatch error may be based around the standard deviation of the image frames in the cardiac cycle rather than the sum of square error. Including image frames based on the standard deviation provides insight into the content of the information that is removed when several image frames are synthesized to form an image frame in the cineloop. Using the mismatch error based on the standard deviation, a cineloop may be constructed to visualize this information. Mathematical tools and definitions exist in the literature for quantifying this information. For example, principal component analysis may be used to systematically separate the heartbeats into linear combinations with orthogonal information content.

The cineloop formed by using the standard deviation from the mean will be an image by image display of the variations of the cardiac cycle from a completely repetitive behavior. In tissue velocity imaging the differences may be expressed as the variance and the resulting images may contain values that are proportional to the kinetic energy in the local non-repetitive motion. Information concerning variance from repetitive behavior may be useful in diagnosing several conditions such as arrhythmia and electrophysiological disorders, for example. Additionally, it may be desirable to generate the tissue velocity or strain estimate difference between a single heartbeat and the average for a number of consecutive heartbeats in order to generate a display of early activation in a single heartbeat.

Once each of the image frames in the cardiac cycles have been temporally and spatially aligned, the cineloop is formed. The cineloop is formed by combining the image frames on a pixel-by-pixel basis to form a single resulting cineloop frame. Thus, each pixel in the cineloop image frame may reflect the ultrasound data from each of the selected image frames of the selected cardiac cycles. Additionally, as mentioned above, the data in a particular image frame may be weighted in forming the pixels of the cineloop image frame.

The ultrasound information in the image frames may be combined from the cineloop image frame using various synthesizing techniques known to those skilled in the art. For example, peak detection, mean and median filters may be employed, with or without weighting. Additionally, the efficiency of the combination of the image frames to from the cineloop may be improved by several systems, such as: 1) processing using the non-log compressed data of the ultrasonic signal instead of the log-compressed data; 2) processing using the individual ultrasonic attributes such as tissue intensity, angio, or velocity and then remixing RGB images from the processed versions instead of applying the processing to the original RGB images; 3) processing using correlation coefficients instead of velocities which may, for example, reduce the weight of a velocity estimate in a turbulent flow with a high bandwidth; 4) processing using peak detection which may, for example, highlight regions having a turbulent flow. Processing using peak detection may emphasize jets causes by leakage in valves and make such jets more prominent in a cineloop.

Figure 7:
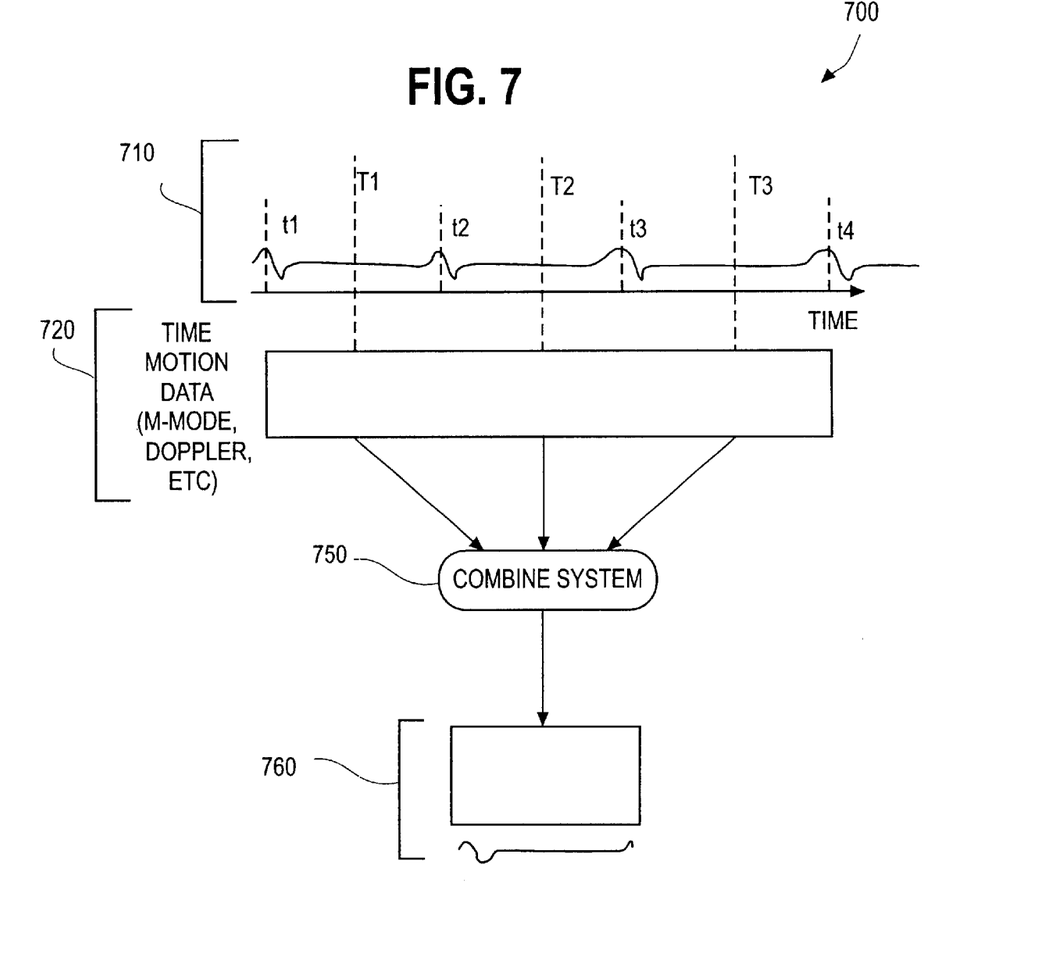
FIG. 7 illustrates an exemplary application of a preferred embodiment of the present invention to time motion ultrasonic data such as M-Mode and PW or CW Doppler.

FIG. 7 illustrates an exemplary application of the present invention to time motion ultrasonic data such as M-Mode and PW or CW Doppler. FIG. 7 includes an imaging sequence diagram 700 which includes an ECG trace 710, a detected near continuous ultrasonic image 720, a combine system 750, and a cineloop 760. Similar to FIG. 1, the ECG trace 710 displays an ECG of three cardiac cycles or heartbeats. As above, the ECG trace 710 includes four trigger events at times (t1, t2, t3 and t4) typically the R-event in the QRS complex, but other events such as the S-event may be employed. The ECG trace 710 also includes three sample events at times (T1, T2, and T3). A time motion ultrasonic image of the heart is obtained at each sample event time T1–T3. As above, the sample events at times (T1, T2, and T3) are selected to be the same time increment from the preceding trigger events at times (t1, t2, t3 and t4) so that the same phase of the cardiac cycle is imaged by each image frame. The three image frames (each, in this case, a line of M-mode data or Doppler data, for example) associated with times (T1, T2, and T3) are then spatially aligned and combined by the align and combine system 750 to form a single image frame of a cineloop 760 of the entire cardiac cycle.

The system of FIG. 7 differs from the system of FIG. 1 in several ways. In the system of FIG. 7, time alignment may be accomplished similarly to the 2-D imaging example of FIG. 1. Alternatively, however, the actual image data in the M-Mode or Doppler display may be used to perform automatic time alignment with, for example, a Viterbi based correlator.

Additionally, in the system of FIG. 7, space alignment may not be possible except as range offsets in M-Mode imaging. To perform spatial alignment, the ultrasonic signal acquisition may be modified to include multiple M-mode lines or multiple Doppler regions of interest. Once the system has been modified to include multiple regions of interest, the regions of interest may then be spatially compared and aligned. Also, the cineloop selecting, weighting, and averaging techniques discussed above for 2-D imaging may also be applied to the time motion system of FIG. 7. Peak detection techniques may be particularly useful in combining Doppler data.

The techniques described above for 2-D imaging may be substantially directly applied for 3-D imaging with a few modifications. First, the spatial alignment may be performed in three dimensions in addition to 2-D. Second, a 3-D system will typically have lower frame rates than a 2-D system. Thus, implementing an ECG trigger reset of the frame acquisition increases in importance for obtaining 3-D image frames having a good temporal alignment.

Figure 8:
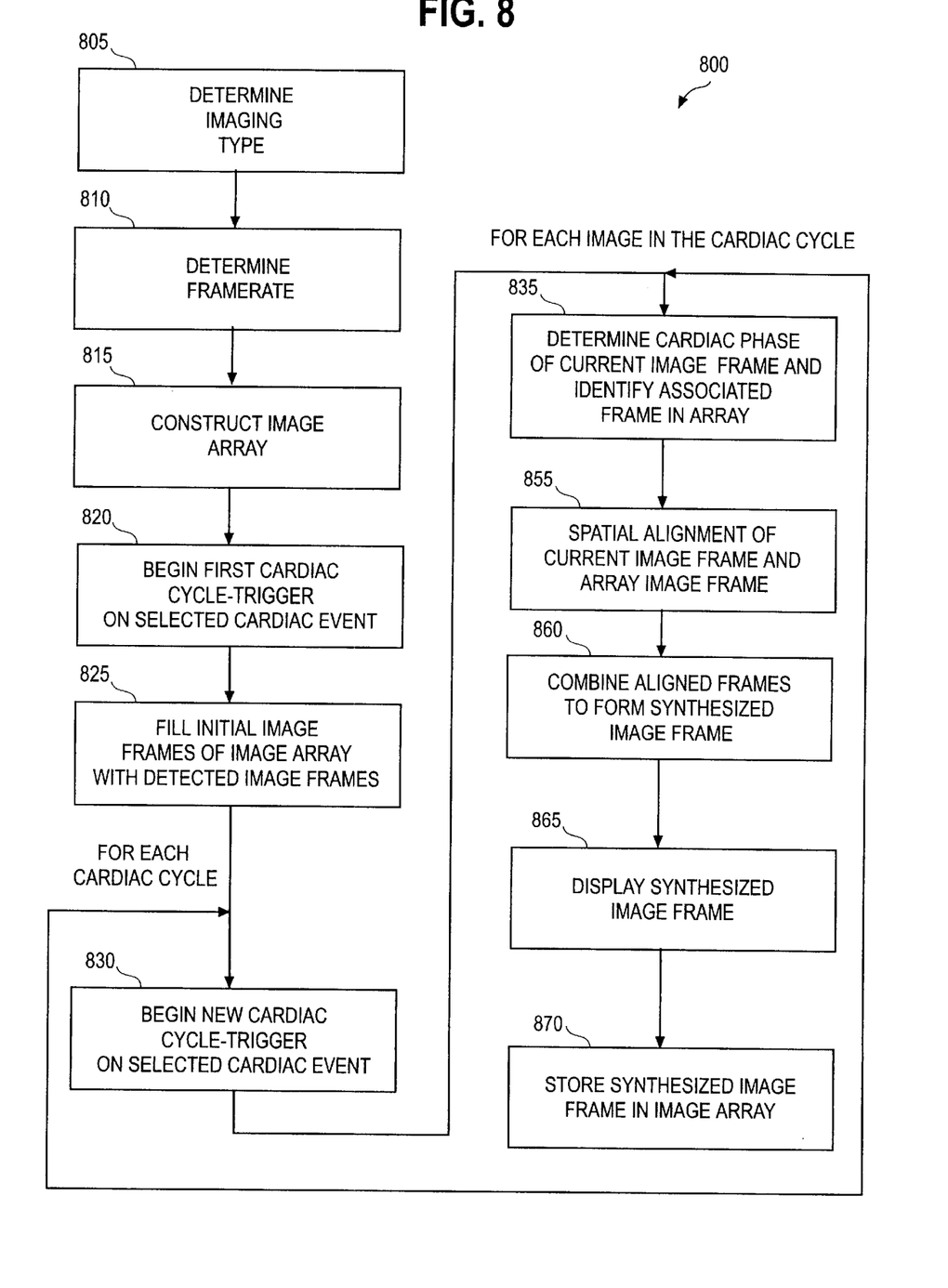
FIG. 8 illustrates a flowchart of a preferred embodiment of the present invention implemented as real-time ultrasonic processing.

Processing steps carried out in a real-time application are illustrated in the flowchart 800 of FIG. 8. First, at step 805, the type of ultrasonic imaging to be performed is determined by the user. Next, at step 810, the maximum frame rate for the particular ultrasonic system performing the particular type of ultrasonic imaging is determined and the desired frame rate (equal to or less then the maximum frame rate) is selected. Alternatively, the framerate may be read from pre-recorded data. Next, at step 815, an image array is initialized or otherwise constructed, such as in a computer memory, for example. At step 820, imaging of the first cardiac cycle begins. As with all of the imaged cardiac cycles, the first cardiac cycle is preferably triggered on a cardiac event such as the R-event. Next, at step 825, the image array is filled with the image frames of the first cardiac cycle.

For instance, once an R-event is triggered, the ultrasound system performs a series of ultrasonic scans of 2D or 3D regions of the patient. The 2D or 3D ultrasound scans are processed and, optionally, scan converted to form 2D or 3D images containing one or more type of ultrasound data, such as B-mode data, color flow data, power doppler data, M-mode data and the like. The 2D or 3D images are stored in cineloop memory in a temporal relation to one another to form a 2D or 3D image sequence. The 2D or 3D image sequence illustrates the tissue and/or blood flow and/or state at a sequence of points in time throughout a cardiac cycle, such as when the heart contracts and expands through a PQRST-complex.

For each successive cardiac cycle, the imaging of the cardiac cycle is triggered on the selected cardiac event at step 830. For each image frame of each successive cardiac cycle, the system performs steps 835–870. First, at step 835, the cardiac phase of the image frame is determined, possibly by determining the time since the R-event selected as the trigger for the cardiac cycle, and in associated frame in the array is determined. The associated frame may be determined to be the frame in the array with the most similar cardiac phase to the current image frame. Then, at step 855, the current frame is optionally spatially aligned with the image frame from the image array that was chosen at step 835. Spatial alignment is optional, but improves performance when the image of the heart may have shifted between heart cycles. Next, at step 860, the spatially and temporally aligned current image frame and array image frame are combined to form a synthesized image frame. The frames may be weighted as described above. Then, at step 865, the synthesized image frame may be optionally displayed for real-time viewing. Finally, at step 870, the synthesized frame is stored in the image array in place of the original array image frame.

Figure 9:
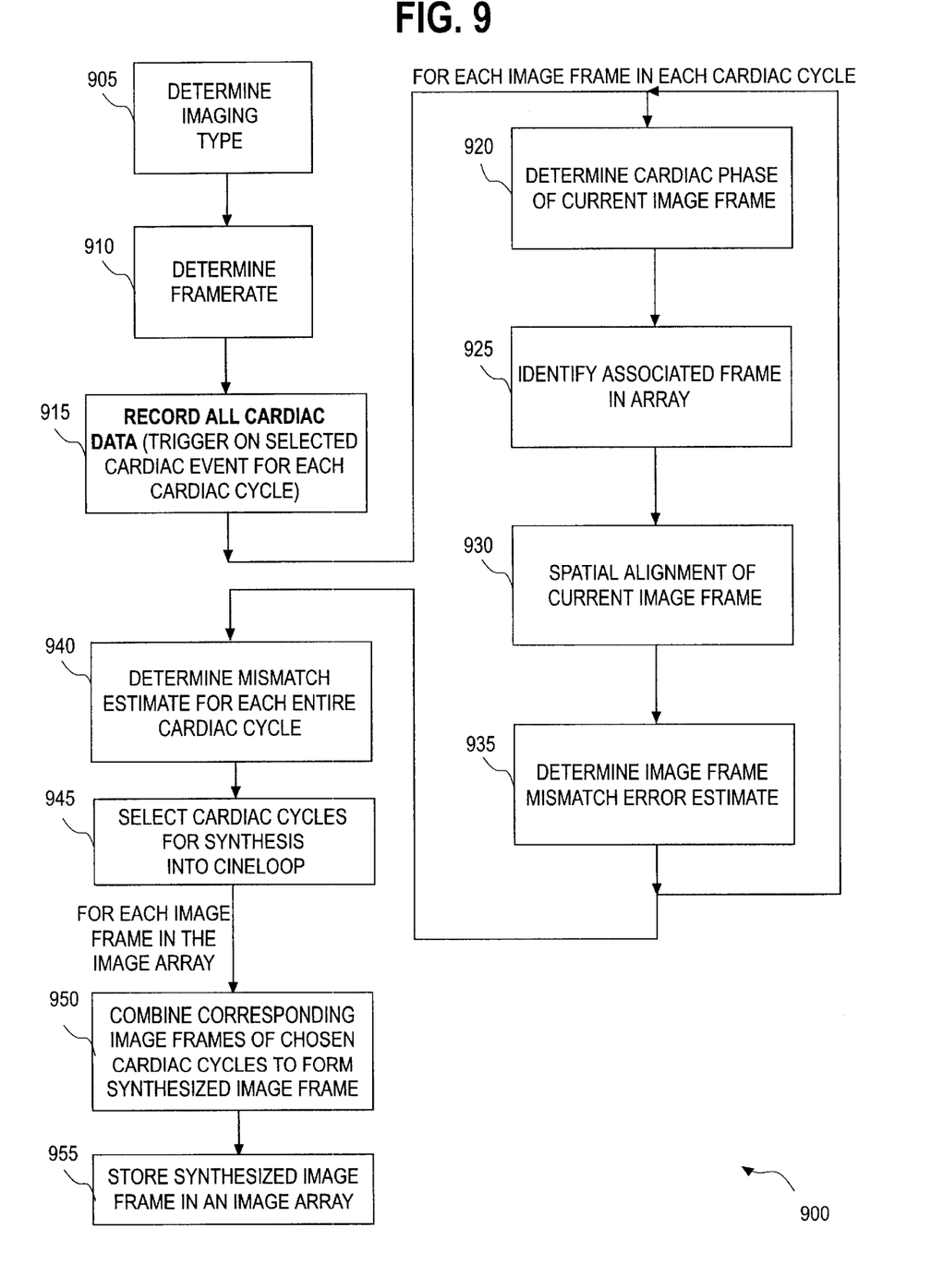
FIG. 9 illustrates a flowchart of a preferred embodiment of the present invention implemented as processing of a recorded ultrasonic sequence.

The processing of a recorded sequence of multiple cardiac cycles of ultrasonic images is further illustrated in the flowchart 900 of FIG. 9. First, at step 905, the type of ultrasonic imaging to be performed is determined by the user as in FIG. 8. Next, at step 910, the maximum frame rate for the particular ultrasonic system performing the particular type of ultrasonic imaging is determined and the desired frame rate (equal to or less then the maximum frame rate) is selected. Then, at step 915, the ultrasonic cardiac images are recorded. Clinically, the patient is typically instructed to breathe our and wait. Once the patient has completed breathing out, the system images several heart cycles and then ceases imaging, at which point the patient begins breathing again normally. The captured heart cycles are then typically processed and analyzed.

For each cardiac cycle, the ultrasonic imaging is triggered on the selected cardiac event, as described above. Then, steps 920–935 take place for each image frame in each cardiac cycle. First, at step 920, the cardiac phase of the image frame is determined, possibly by determining the time since the R-event selected as the trigger for the cardiac cycle. At step 925, an associated frame in the array is identified. The associated frame may be determined to be the frame in the array with the most similar cardiac phase to the current image frame. The current image frame may also be temporally aligned, for example by linear stretching, as discussed above. Next, at step 930, the current image frame is optionally spatially aligned. Then, at step 935, the mismatch error estimate for the current image frame is optionally determined. Once a mismatch error estimate has been determined for each image frame in a cardiac cycle, the mismatch estimate for the entire cardiac cycle may be optionally determined at step 940. Then, at step 945, the cardiac cycles to be synthesized to form the cineloop are selected. The selected cardiac cycles may be those cycles having the lowest mismatch error, for example. Alternatively, a selected number (such as three or seven) of the most recently recorded cycles may be selected. The number of heart cycles to include may be externally selected by a user. Next, for each image frame to be included in the cineloop, the corresponding image frames of each selected cardiac cycle are synthesized to from a synthesized image frame in the image array of the cineloop at step 950. Finally, at step 955, the synthesized image frame is stored in the image array. Once all the image frames have been stored in the image array, the cineloop is complete.

As mentioned above, although in the present exemplary case the heart is imaged, the present invention is not limited to the heart and may be useful in the imaging of many features, especially where the imaged feature has a periodic behavior that follows the cardiac cycle such as vascular and blood flow studies in various organs, for example. The present invention may also be applied to any imaging mode including existing applications such as tissue/B-mode imaging, color flow imaging, angio/Power Doppler imaging, tissue motion or velocity imaging and strain rate imaging or time mode imaging, M-mode or PV or CV Doppler, or other ultrasonic imaging modes.

Also, as mentioned above, the present invention combines corresponding instants in different cardiac cycles to form a cineloop, rather than combining consecutive measurements representing different instants in the cardiac cycle. In addition, in the current invention different images of the cardiac cycle are generally uncorrelated in terms of the ultrasound imaging system. The recorded data corresponding to actual heart motion may be correlated in processing due to the repetitive motion of the heart. However, the noise content of the ultrasonic images, such as speckle patterns, remains uncorrelated. Combining ultrasonic images with uncorrelated noise content may significantly reduce the overall noise content and yield an improved signal-to-noise ratio. The present invention provides strong noise suppression without degrading the dynamics of the imaged organ.

Figure 10:
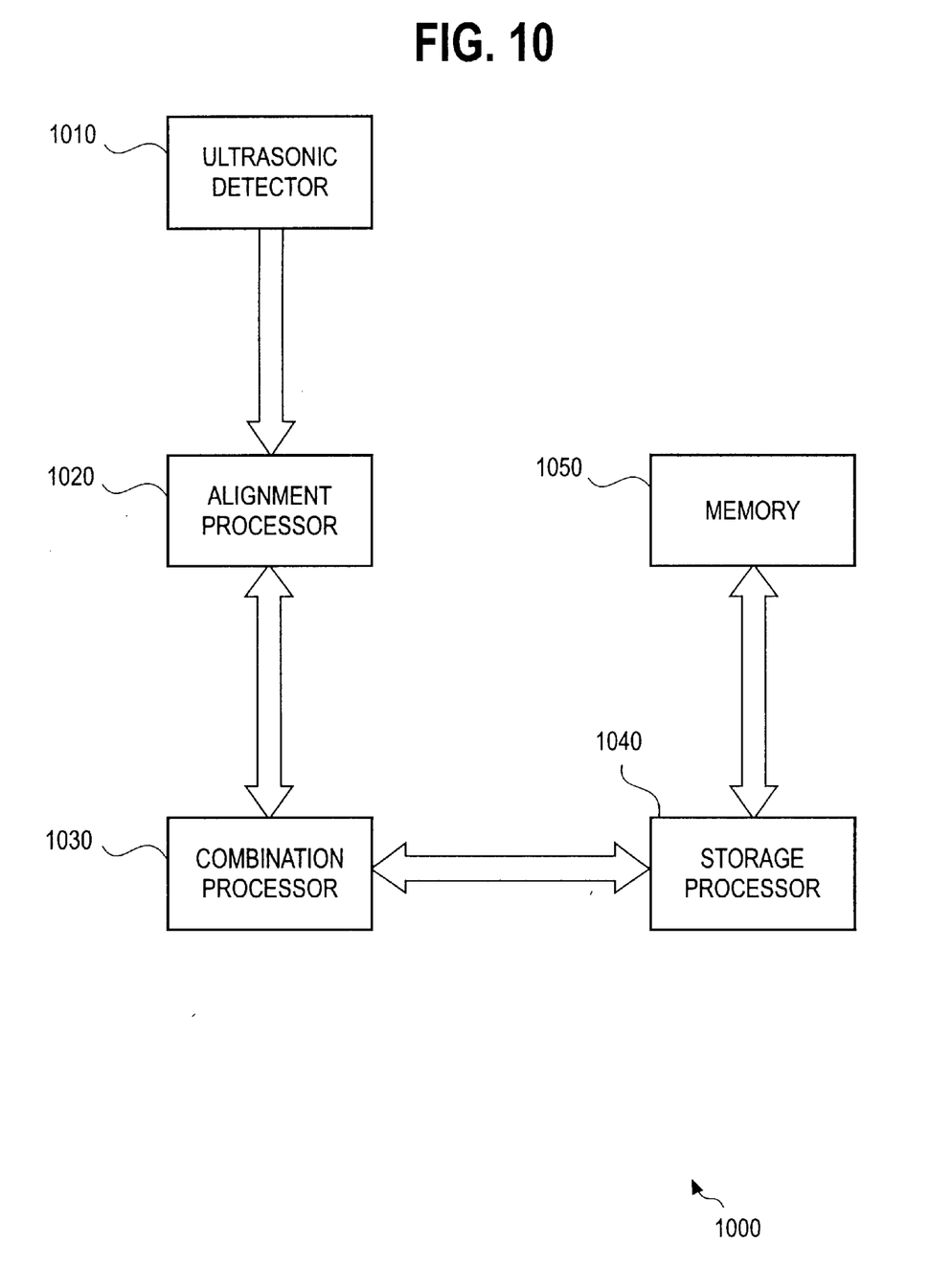
FIG. 10 illustrates a preferred embodiment of an ultrasonic apparatus performing the present invention.

FIG. 10 illustrates a preferred embodiment of an ultrasonic apparatus 1000 performing the present invention. The ultrasonic apparatus 1000 includes an ultrasonic detector 1010, an alignment processor 1020, a combination processor 1030, a storage processor 1040, and a memory 1050. In operation, the ultrasonic detector 1010 detects at least a first series of image frames and a second series of image frames. As discussed above, the first series of image frames may simply pass through without processing the alignment processor 1020, the combination processor 1030 and the storage processor 1040 to the memory 1050 where they may be stored. Once the second series of ultrasonic image frames is detected, each image frame, as it is detected, is passed from the ultrasonic detector 1010 to the alignment processor 1020. The alignment processor 1020 retrieves, from the memory 1050, an image frame having a similar cardiac cycle phase as described above. The alignment processor 1020 then aligns the detected image frame and the retrieved image frame both spatially and temporally and passes both frames to the combination processor 1030. The combination processor 1030 combines the two aligned image frames to form a synthesized image frame and passes the synthesized image frame to the storage processor 1040. The storage processor 1040 then stores the synthesized image frame in the memory 1050.

While particular elements, embodiments and applications of the present invention have been shown and described, it is understood that the invention is not limited thereto since modifications may be made by those skilled in the art, particularly in light of the foregoing teaching. It is therefore contemplated by the appended claims to cover such modifications and incorporate those features which come within the spirit and scope of the invention.

What is claimed is:

1. An ultrasonic imaging system for synthesizing a cineloop of compounded ultrasonic images including:
    an ultrasonic detector for detecting at least first and second series of image frames;
    a memory for storing at least one series of image frames;
    an alignment processor for determining phases of the image frames of said first and second series of image frames and identifying associated frames in said first and second series;
    a combination processor for combining associated image frames from said first and second series of image frames to form a combined image frame; and
    a storage processor for storing combined image frames in said memory.

2. The system of claim 1 wherein said ultrasonic detector is triggered on a selected physiological event.

3. The system of claim 1 wherein said physiological event is the R-event of the cardiac cycle.

4. The system of claim 1 further comprising:
    performing at least one of temporal and spatial alignment of the image frames of said first and second series of image frames.

5. The system of claim 1 wherein the ultrasonic image frames are cardiac image frames and are displayed in real-time before storing.

6. The system of claim 1 wherein at least one of said ultrasonic image frames of said image array is associated with an age attribute based on the time since said image frame was stored in said image array.

7. The system of claim 6 wherein said combination processor includes said age attribute as a weighting factor in combining aligned image frames.

8. The system of claim 1 wherein said alignment processor performs linear stretching to temporally align image frames.

9. The system of claim 1 wherein said alignment processor performs spatial alignment by minimizing the square error between image frames.

10. The system of claim 1 wherein the alignment processor interpolates a spatial alignment for all image frames in a series of image frames based on a spatial alignment of less than all image frames in said series of image frames.

11. The system of claim 1 further including a detector for detecting an atypical image frame series and excluding said atypical image frame series from combination.

12. The system of claim 1 further including a mismatch error processor for generating a mismatch error estimate based on the mismatch error between at least one of the temporal and spatial alignment of image frames of different series.

13. The system of claim 12 wherein said mismatch error processor excludes image frame series having a mismatch error estimate above a predetermined level from combination.

14. The system of claim 12 wherein said mismatch error processor excludes a fraction of the image frame series having greater mismatch error estimates from combination.

15. The system of claim 12 wherein said mismatch error is based on the standard deviation between at least one of the temporal and spatial alignment of image frames of different series.

16. A method for synthesizing a series of compounded ultrasonic images comprising the steps of:
   forming an image array in memory, said image array having a series of image frames;
   initializing a first series of image frames in said memory from detected ultrasonic signals of a first cardiac cycle;
   detecting an image frame of a subsequent cardiac cycle;
   determining the cardiac phase of said image frame;
   associating said image frame with a corresponding image frame in said array;
   combining said detected frame and said associated array frame to form a synthesized image frame; and
   storing said series of synthesized image frame in said image array.

17. The method of claim 16 wherein said first series of image frames and said second series of image frames are triggered on a selected physiological event.

18. The method of claim 16 further comprising:
   determining a maximum frame rate based on at least one of the type of ultrasonic imaging to be performed and the specific ultrasonic system performing the imaging; and
   determining the number of image frames in said image array to be less than or equal to the number of image frames permitted by said maximum frame rate.

19. The method of claim 16 wherein the ultrasonic image frames are cardiac image frames and are displayed in real-time.

20. The method of claim 16 wherein at least one of said ultrasonic image frames of said image array is associated with an age attribute based on the time since said image frame was stored in said image array.

21. The method of claim 20 wherein said combining step further includes said age attribute as a weighting factor in combining aligned image frames.

22. The method of claim 16 wherein said aligning step performs further includes linear stretching to temporally align image frames.

23. The method of claim 16 wherein said aligning step further includes performs spatial alignment by minimizing the square error between image frames.

24. The method of claim 16 wherein the aligning step further includes interpolates a spatial alignment for all image frames in a series of image frames based on a spatial alignment of less than all image frames in said series of image frames.

25. The method of claim 16 further including detecting an atypical image frame series and excluding said atypical image frame series from combination.

26. The method of claim 16 further including generating a mismatch error estimate based on the mismatch error between at least one of the temporal and spatial alignment of image frames of different series.

27. The method of claim 26 wherein further including excluding from combination an image frame series having a mismatch error estimate above a predetermined level.

28. The method of claim 26 further including excluding a fraction of the image frame series having greater mismatch error estimates from combination.

29. The method of claim 26 wherein said mismatch error is based on the standard deviation between at least one of the temporal and spatial alignment of image frames of different series.

30. A method for synthesizing a series of compounded ultrasonic images comprising the steps of:
   recording at least a first and second series of image frames from detected ultrasonic signals;
   determining corresponding cardiac phases in a cardiac cycle for a plurality of image frames of at least one series;
   selecting at least two of said first and second series of image frames;
   combining said at least two image frames to form a synthesized image frame; and
   storing said synthesized image frame in an image array.

31. The method of claim 30 wherein said recording of series of image frames is triggered on a selected physiological event.

32. The method of claim 30 further comprising:
   determining a maximum frame rate based on at least one of the type of ultrasonic imaging to be performed and the specific ultrasonic system performing the imaging; and
   determining the number of image frames in said image array to be less than or equal to the number of image frames permitted by said maximum frame rate.

33. The method of claim 30 wherein the ultrasonic image frames are cardiac image frames and are displayed in real-time.

34. The method of claim 30 wherein at least one of said ultrasonic image frames of said image array is associated with an age attribute based on the time since said image frame was stored in said image array.

35. The method of claim 34 wherein said combining step further includes said age attribute as a weighting factor in combining aligned image frames.

36. The method of claim 30 wherein said temporal alignment further includes linear stretching to temporally align image frames.

37. The method of claim 30 further including determining at least one of a temporal alignment, a spatial alignment, and a mismatch error for a plurality of image frame of at least one series.

38. The method of claim 37 wherein said spatial alignment further includes interpolating a spatial alignment for all image frames in a series of image frames based on a spatial alignment of less than all image frames in said series of image frames.

39. The method of claim 30 further including detecting an atypical image frame series and excluding said atypical image frame series from combination.

40. The method of claim 37 further including generating a mismatch error estimate based on the mismatch error between at least one of the temporal and spatial alignment of image frames of different series.

41. The method of claim 40 wherein further including excluding from combination an image frame series having a mismatch error estimate above a predetermined level.

42. The method of claim 40 further including excluding a fraction of the image frame series having greater mismatch error estimates from combination.

43. The method of claim 40 wherein said mismatch error is based on the standard deviation between at least one of the temporal and spatial alignment of image frames of different series.

44. The method of claim 37 further including performing spatial alignment by minimizing the square error between image frames.

45. An ultrasonic imaging system for synthesizing a cineloop of compounded ultrasonic images of a cardiac cycle including:
- an ultrasonic detector for detecting a series of images from ultrasonic signals of a cardiac cycle; and
- a processor for synthesizing said series of images into a cineloop of compounded ultrasonic images of said cardiac cycle.

46. A method for synthesizing a cineloop of compounded ultrasonic images of a cardiac cycle including:
- detecting a series of images from ultrasonic signals of a cardiac cycle with an ultrasonic detector; and
- synthesizing said series of images into a cineloop of compounded ultrasonic images of said cardiac cycle through said processor.

47. An ultrasonic imaging system for synthesizing a cineloop of compounded ultrasonic images of an anatomical structure including:
- an ultrasonic detector for detecting a series of images from ultrasonic signals of said anatomical structure; and
- a processor for synthesizing said series of images into a cineloop of compounded ultrasonic images of said anatomical structure.

48. A method for synthesizing a cineloop of compounded ultrasonic images of an anatomical structure including:
- detecting a series of images from ultrasonic signals of an anatomical structure with an ultrasonic detector; and
- synthesizing said series of images into a cineloop of compounded ultrasonic images of said cardiac cycle through said processor.

49. A system for initiating an acquisition of a cineloop based on a cardiac event including a detector for acquiring a series of ultrasonic signals, wherein the initiation of the acquisition of said series of ultrasonic signals is based on a cardiac event.

50. A method of initiating an acquisition of a cineloop based on a cardiac event including:
- detecting a cardiac event with a detector; and
- initiating the acquisition of a series of ultrasonic signals based on said cardiac event.

51. A system for initiating an acquisition of a cineloop based on a physiological event including a detector for acquiring a series of ultrasonic signals, wherein the initiation of the acquisition of said series of ultrasonic signals is based on a physiological event.

52. The system of claim 51 wherein said physiological event is a cardiac event.

53. A method of initiating an acquisition of a cineloop based on a physiological event including:
- detecting a physiological event with a detector; and
- initiating the acquisition of a series of ultrasonic signals based on said physiological event.

54. A method of constructing a series of ultrasonic image frames including the step of determining a cardiac phase of an image frame within said series.

55. A system for constructing a series of compounded ultrasonic image frames including a processor for determining a cardiac phase of an image frame within said series.

56. A system for synthesizing a series of compounded ultrasonic images including a processor for associating individual frames within a first series of image frames with individual frames within a second series of image frames to allow synthesis of a compound ultrasonic image of said first and second series of image frames.

57. The system of claim 56 wherein said processor associates said individual frames within said first series with said individual frames within said second series based on a physiological event.

58. The system of claim 56 wherein said processor associates said individual frames within said first series with said individual frames within said second series based on a phase of a cardiac cycle.

59. A method of synthesizing a series of compounded ultrasonic images including the step of associating individual frames within a first series of image frames with individual frames within a second series of image frames to allow synthesis of a compound ultrasonic image of said first and second series of image frames.

60. The method of claim 57 wherein said associating step includes associating individual frames within a first series of images frames with individual frames within a second series of images frames based on a physiological event.

61. The method of claim 57 wherein said associating step includes associating individual frames within a first series of images frames with individual frames within a second series of images frames based on a phase of a cardiac cycle.

62. A method of constructing a cineloop of ultrasonic images of a physiological cycle including the step of positioning said images in said cineloop based on the phase of said physiological cycle.

63. A method of constructing a cineloop of ultrasonic images of an physiological cycle wherein the length of said cineloop is automatically controlled to be a single physiological cycle.

* * * * *